United States Patent [19]

Sanchez-Pescador et al.

[11] Patent Number: 5,618,674
[45] Date of Patent: Apr. 8, 1997

[54] CHLAMYDIAE PROBES FOR USE IN SOLUTION PHASE SANDWICH HYBRIDIZATION ASSAYS

[75] Inventors: Ray Sanchez-Pescador, San Leandro; Diana J. Besemer, Albany; Michael S. Urdea, Alamo, all of Calif.

[73] Assignee: Chiron Corporation, Emeryville, Calif.

[21] Appl. No.: 479,487

[22] Filed: Jun. 7, 1995

Related U.S. Application Data

[63] Continuation of Ser. No. 813,587, Dec. 23, 1991, abandoned.

[51] Int. Cl.$^6$ .............................. C12Q 1/68; C12P 19/34; C07H 21/04; C12N 15/00
[52] U.S. Cl. .................. 435/6; 435/91.1; 435/91.2; 536/23.1; 536/24.3; 536/24.32; 536/24.33; 536/25.3; 935/8; 935/77; 935/78
[58] Field of Search ............. 435/6, 91.1, 91.2; 536/23.1, 24.3, 24.32, 24.33, 25.3; 935/8.77, 78; 436/94

[56] References Cited

U.S. PATENT DOCUMENTS

| | | | |
|---|---|---|---|
| 4,731,325 | 3/1988 | Palva et al. | 435/6 |
| 4,868,105 | 9/1989 | Urdea et al. | 435/6 |
| 5,124,246 | 6/1992 | Urdea et al. | |

FOREIGN PATENT DOCUMENTS

| | | |
|---|---|---|
| 0361983 | 4/1989 | European Pat. Off. . |
| 0317077 | 5/1989 | European Pat. Off. . |
| 0336412 | 10/1989 | European Pat. Off. . |
| 0420260 | 4/1991 | European Pat. Off. . |
| WO88/03957 | 6/1988 | WIPO . |
| WO90/15159 | 12/1990 | WIPO . |

OTHER PUBLICATIONS

Sommer and Tantz, *Nucleic Acids Research*, vol. 17, No. 16, 1989, p. 6749.

Palmer, L.; Falkow, S. A common plasmid of *Chlamydia trachomatis*. Plasmid 16:52–62; 1986.

*Primary Examiner*—Bradley L. Sisson
*Attorney, Agent, or Firm*—Tyler Dylan; Kenneth M. Goldman; Robert P. Blackburn

[57] ABSTRACT

Novel DNA probe sequences for detection of Chlamydiae in a sample in a solution phase sandwich hybridization assay are described. Amplified nucleic acid hybridization assays using the probes are exemplified.

20 Claims, No Drawings

CHLAMYDIAE PROBES FOR USE IN SOLUTION PHASE SANDWICH HYBRIDIZATION ASSAYS

This application is a continuation of U.S. application Ser. No. 07/813,587, filed Dec. 23, 1991, now abandoned.

TECHNICAL FIELD

This invention is in the field of nucleic acid hybridization assays. More specifically, it relates to novel nucleic acid probes for detecting Chlamydiae.

BACKGROUND ART

*Chlamydia trachomatis* is a major human pathogen responsible for such diseases as trachoma, inclusion conjunctivitis, pneumonia, lymphogranuloma venereum, and mucous membrane genital tract infections such as cervicitis and urethritis. The latter infections may develop systemic complications resulting in epididymitis, salpingitis, or perihepatitis.

U.S. Pat. No. 4,731,325, issued Mar. 15, 1988, discloses the use of cloned Chlamydiae-specific DNA for use as a probe in a sandwich hybridization assay.

PCT WO 88/03957, filed Nov. 24, 1987, discloses rRNA sequences for use as probe in hybridization assays for *C. trachomatis*. EPA 0 361 983, filed Oct. 2, 1989, discloses rRNA sequences for use as RNA template end-linked probe constructs for the detection of *C. trachomatis* in hybridization assays. PCT WO 90/15159, filed May 31, 1990, discloses rRNA probes and methods utilizing such probes to detect *C. trachomatis* in clinical samples.

EPA 0336 412 A2, filed Apr. 6, 1989, discloses synthetic oligonucleotides derived from the *C. trachomatis* plasmid PCHL1 for use as hybridization probes to detect *C. trachomatis*.

EPA 0 420 260 A2, filed Sep. 29, 1989, discloses capture probes and polymerase chain reaction primers designed from the nucleotide sequence of the cryptic plasmid of the *C. trachomatis* L1 serovar Commonly owned U.S. Ser. No. 07/691,639, filed Apr. 25, 1991, discloses polynucleotides of the major outer membrane protein of *C. trachomatis* that may be used as hybridization probes to detect Chlamydiae.

Commonly owned U.S. Pat. No. 4,868,105, issued Sep. 19, 1989, describes a solution phase nucleic acid sandwich hybridization assay in which analyte nucleic acid is first hybridized in solution to a labeling probe set and to a capturing probe set in a first vessel. The probe-analyte complex is then transferred to a second vessel that contains a solid-phase-immobilized probe that is substantially complementary to a segment of the capturing probes. The segments hybridize to the immobilized probe, thus removing the complex from solution. Having the analyte in the form of an immobilized complex facilitates subsequent separation steps in the assay. Ultimately, single stranded segments of the labeling probe set are hybridized to labeled probes, thus permitting the analyte-containing complex to be detected via a signal generated directly or indirectly from the label.

Commonly owned EPA 883096976 discloses a variation in the assay described in U.S. Pat. No. 4,868,105, issued Sep. 19, 1989, in which the signal generated by the labeled probes is amplified. The amplification involves the use of nucleic acid multimers. These multimers are branched polynucleotides that are constructed to have a segment that hybridizes specifically to the analyte nucleic acid or to a nucleic acid (branched or linear) that is bound to the analyte and iterations of a second segment that hybridize specifically to the labeled probe. In the assay employing the multimer, the initial steps of hybridizing the analyte to label or amplifier probe sets and capturing probe sets in a first vessel and transferring the complex to another vessel containing immobilized nucleic acid that will hybridize to a segment of the capturing probes are followed. The multimer is then hybridized to the immobilized complex and the labeled probes in turn hybridized to the second segment iterations on the multimer. Since the multimers provide a large number of sites for label probe attachment, the signal is amplified. Amplifier and capture probe sequences are disclosed for Hepatitis B virus, *Neisseria gonorrhoeae*, penicillin and tetracycline resistance in *N. gonorrhoeae*, and *C. trachomatis*.

Commonly owned copending application Ser. No. 558, 897, filed Jul. 27, 1990, describes the preparation of large comb-type branched polynucleotide multimers for use in the above-described solution phase assay. The combs provide greater signal enhancement in the assays than the smaller multimers.

DISCLOSURE OF THE INVENTION

One aspect of the invention is a synthetic oligonucleotide useful as an amplifier probe in a sandwich hybridization assay for Chlamydiae comprising a first segment having a nucleotide sequence substantially complementary to a segment of Chlamydiae DNA and a second segment having a nucleotide sequence substantially complementary to an amplifier multimer.

Another aspect of the invention is a synthetic oligonucleotide useful as a capture probe in a sandwich hybridization assay for Chlamydiae comprising a first segment having a nucleotide sequence substantially complementary to a segment of Chlamydiae DNA and a second segment having a nucleotide sequence substantially complementary to an oligonucleotide bound to a solid phase.

Another aspect of the invention is a solution sandwich hybridization assay for detecting the presence of Chlamydiae in a sample, comprising
(a) contacting the sample under hybridizing conditions with an excess of (i) an amplifier probe oligonucleotide comprising a first segment having a nucleotide sequence substantially complementary to a segment of Chlamydiae DNA and a second segment having a nucleotide sequence substantially complementary to an oligonucleotide unit of a nucleic acid multimer and (ii) a capture probe oligonucleotide comprising a first segment having a nucleotide sequence that is substantially complementary to a segment of Chlamydiae DNA and a second segment that is substantially complementary to an oligonucleotide bound to a solid phase;
(b) contacting the product of step (a) under hybridizing conditions with said oligonucleotide bound to the solid phase;
(c) thereafter separating materials not bound to the solid phase;
(d) contacting the product of step (c) under hybridization conditions with the nucleic acid multimer, said multimer comprising at least one oligonucleotide unit that is substantially complementary to the second segment of the amplifier probe polynucleotide and a multiplicity of second oligonucleotide units that are substantially complementary to a labeled oligonucleotide;

(e) removing unbound multimer;
(f) contacting under hybridizing conditions the solid phase complex product of step (e) with the labeled oligonucleotide;
(g) removing unbound labeled oligonucleotide; and
(h) detecting the presence of label in the solid phase complex product of step (g).

Another aspect of the invention is a kit for the detection of Chlamydiae in a sample comprising in combination
(i) a set of amplifier probe oligonucleotides wherein the amplifier probe oligonucleotide comprises a first segment having a nucleotide sequence substantially complementary to a segment of Chlamydiae DNA and a second segment having a nucleotide sequence substantially complementary to an oligonucleotide unit of a nucleic acid multimer;
(ii) a set of capture probe oligonucleotides wherein the capture probe oligonucleotide comprises a first segment having a nucleotide sequence that is substantially complementary to a segment of Chlamydiae DNA and a second segment that is substantially complementary to an oligonucleotide bound to a solid phase;
(iii) a nucleic acid multimer, said multimer comprising at least one oligonucleotide unit that is substantially complementary to the second segment of the amplifier probe polynucleotide and a multiplicity of second oligonucleotide units that are substantially complementary to a labeled oligonucleotide; and
(iv) a labeled oligonucleotide.

MODES FOR CARRYING OUT THE INVENTION

Definitions

"Solution phase nucleic acid hybridization assay" intends the assay techniques described and claimed in commonly owned U.S. Pat. No. 4,868,105 and EPA 883096976 which published as EP 0317077 on May 24, 1989, the disclosure of which is also found in U.S. Pat. No. 5,124,246 which issued on Jun. 23, 1992.

A "modified nucleotide" intends a nucleotide monomer that may be stably incorporated into a polynucleotide and which has an additional functional group. Preferably, the modified nucleotide is a 5'-cytidine in which the $N^4$-position is modified to provide a functional hydroxy group.

An "amplifier multimer" intends a linear or branched polynucleotide that is capable of hybridizing simultaneously directly or indirectly to analyte nucleic acid and to a multiplicity of polynucleotide iterations (i.e., either iterations of another multimer or iterations of a labeled probe). The branching in the multimers is effected through covalent bonds and the multimers are composed of two types of oligonucleotide units that are capable of hybridizing, respectively, to analyte nucleic acid or nucleic acid hybridized to analyte nucleic acid and to a multiplicity of labeled probes. The composition and preparation of such multimers are described in EPA 883096976 and U.S. Ser. No. 558,897 filed Jul. 27, 1990, the disclosures of which are incorporated herein by reference.

The term "amplifier probe" is intended as a branched or linear polynucleotide that is constructed to have a segment that hybridizes specifically to the analyte nucleic acid and a segment or iterations of a segment that hybridize specifically to an amplifier multimer.

The term "capture probe" is intended as an oligonucleotide having a segment substantially complementary to a nucleotide sequence of the target DNA and a segment that is substantially complementary to a nucleotide sequence of a solid-phase-immobilized probe.

"Large" as used herein to describe the comb-type branched polynucleotides of the invention intends a molecule having at least about 15 branch sites and at least about 20 iterations of the labeled probe binding sequence.

"Comb-type" as used herein to describe the structure of the branched polynucleotides of the invention intends a polynucleotide having a linear backbone with a multiplicity of sidechains extending from the backbone.

A "cleavable linker molecule" intends a molecule that may be stably incorporated into a polynucleotide chain and which includes a covalent bond that may be broken or cleaved by chemical treatment or physical treatment such as by irradiation.

All nucleic acid sequences disclosed herein are written in a 5' to 3' direction. Nucleotides are designated according to the nucleotide symbols recommended by the IUPAC-IUB Biochemical Nomenclature Commission.

Solution Phase Hybridization Assay

The general protocol for the solution phase sandwich hybridizations is as follows. The analyte nucleic acid is placed in a microtiter well with an excess of two single-stranded nucleic acid probe sets: (1) a set of capture probes, each having a first binding sequence substantially complementary to the analyte and a second binding sequence that is substantially complementary to nucleic acid bound to a solid support, for example, the well surface or a bead, and (2) a set of amplifier probes (branched or linear), each having a first binding sequence that is capable of specific binding to the analyte and a second binding sequence that is capable of specific binding to a segment of the multimer. The resulting product is a three component nucleic acid complex of the two probes hybridized to the analyte by their first binding sequences. The second binding sequences of the probes remain as single-stranded segments as they are not complementary to the analyte. This complex hybridizes to the immobilized probe on the solid surface via the second binding sequence of the capture probe. The resulting product comprises the complex bound to the solid surface via the duplex formed by the oligonucleotide bound to the solid surface and the second binding sequence of the capture probe. Unbound materials are then removed from the surface such as by washing.

The amplification multimer is then added to the bound complex under hybridization conditions to permit the multimer to hybridize to the available second binding sequence(s) of the amplifier probe of the complex. The resulting complex is then separated from any unbound multimer by washing. The labeled oligonucleotide is then added under conditions which permit it to hybridize to the substantially oligonucleotide units of the multimer. The resulting immobilized labeled nucleic acid complex is then washed to remove unbound labeled oligonucleotide, and read.

The analyte nucleic acids may be from a variety of sources, e.g., biological fluids or solids, and may be prepared for the hybridization analysis by a variety of means, e.g., proteinase K/SDS, chaotropic salts, etc. Also, it may be of advantage to decrease the average size of the analyte nucleic acids by enzymatic, physical or chemical means, e.g., restriction enzymes, sonication, chemical degradation (e.g., metal ions), etc. The fragments may be as small as 0.1 kb, usually being at least about 0.5 kb and may be 1 kb or higher. The analyte sequence is provided in single-stranded form for analysis. Where the sequence is naturally present in single-stranded form, denaturation will not be required. However, where the sequence may be present in double-stranded form, the sequence should be denatured. Denaturation can be carried out by various techniques, such as alkali, generally from about 0.05 to 0.2M hydroxide, formamide, salts, heat, enzymes, or combinations thereof.

The first binding sequences of the capture probe and amplifier probe that are substantially complementary to the analyte sequence will each be of at least 15 nucleotides, usually at least 25 nucleotides, and not more than about 5 kb, usually not more than about 1 kb, preferably not more than about 100 nucleotides. They will typically be approximately 30 nucleotides. They will normally be chosen to bind to different sequences of the analyte. The first binding sequences may be selected based on a variety of considerations. Depending upon the nature of the analyte, one may be interested in a consensus sequence, a sequence associated with polymorphisms, a particular phenotype or genotype, a particular strain, or the like.

The number of different amplifier and capture probes used influences the sensitivity of the assay, because the more probe sequences used, the greater the signal provided by the assay system. Furthermore, the use of more probe sequences allows the use of more stringent hybridization conditions, thereby reducing the incidence of false positive results. Thus, the number of probes in a set will be at least one capture probe and at least one amplifier probe, more preferably two capture and two amplifier probes, and most preferably 5–100 capture probes and 5–100 amplifier probes.

Oligomeric probes specific for Chlamydiae were designed as described in EPA 883096976 which published as EP 0317077 on May 24, 1989, the disclosure of which is also found in U.S. Pat. No. 5,124,246 which issued on Jun. 23, 1992, from the Chlamydiae pCHL2 plasmid (Palmer and Falkow, *Plasmid*, 16:52–62, 1986). In the instant invention, additional probes were designed from other regions of the plasmid, the improvement being additional sensitivity in the assay as more capture probe sequences are available to detect the presence of the test organism.

The arrangement of label and capture sequences may vary from interspersing capture and label sequences to clustering the capture or label sequences together. In the experimental examples described below, the capture probes are interspersed with the label probes, but one of ordinary skill in the art would recognize that this is not a necessary limitation in the design of the probe sets.

The second binding sequences of the capture probe and amplifier probe are selected to be substantially complementary, respectively, to the oligonucleotide bound to the solid surface and to a segment of the multimer and so as to not be encountered by endogenous sequences in the sample/analyte. The second binding sequence may be contiguous to the first binding sequence or be spaced therefrom by an intermediate noncomplementary sequence. The probes may include other noncomplementary sequences if desired. These noncomplementary sequences must not hinder the binding of the binding sequences or cause nonspecific binding to occur.

The capture probe and amplifier probe may be prepared by oligonucleotide synthesis procedures or by cloning, preferably the former.

It will be appreciated that the binding sequences need not have perfect complementarity to provide homoduplexes. In many situations, heteroduplexes will suffice where fewer than about 10% of the bases are mismatches, ignoring loops of five or more nucleotides. Accordingly, as used herein the term "complementary" intends exact complementarity wherein each base within the binding region corresponds exactly, and "substantially complementary" intends 90% or greater homology.

The labeled oligonucleotide will include a sequence substantially complementary to the repeated oligonucleotide units of the multimer. The labeled oligonucleotide will include one or more molecules ("labels"), which directly or indirectly provide a detectable signal. The labels may be bound to individual members of the substantially complementary sequence or may be present as a terminal member or terminal tail having a plurality of labels. Various means for providing labels bound to the oligonucleotide sequences have been reported in the literature. See, for example, Leary et al., *Proc. Natl. Acad. Sci. USA* (1983) 80:4045; Renz and Kurz, *Nucl. Acids Res.* (1984) 12:3435; Richardson and Gumport, *Nucl. Acids Res.* (1983) 11:6167; Smith et al., *Nucl. Acids. Res.* (1985) 13:2399; Meinkoth and Wahl, Anal. Biochem. (1984) 138:267. The labels may be bound either covalently or non-covalently to the substantially complementary sequence. Labels which may be employed include radionuclides, fluorescers, chemiluminescers, dyes, enzymes, enzyme substrates, enzyme cofactors, enzyme inhibitors, enzyme subunits, metal ions, and the like. Illustrative specific labels include fluorescein, rhodamine, Texas red, phycoerythrin, umbelliferone, luminol, NADPH, α-β-galactosidase, horseradish peroxidase, alkaline phosphatase, etc.

The ratio of capture probe and amplifier probe to anticipated moles of analyte will each be at least stoichiometric and preferably in excess. This ratio is preferably at least about 1.5:1, and more preferably at least 2:1. It will normally be in the range of 2:1 to $10^6$:1. Concentrations of each of the probes will generally range from about $10^{-5}$ to $10^{-9}$M, with sample nucleic acid concentrations varying from $10^{-21}$ to $10^{-12}$M. The hybridization steps of the assay will generally take from about 10 minutes to 20 hours, frequently being completed in about 1 hour. Hybridization can be carried out at a mildly elevated temperature, generally in the range from about 20° C. to 80° C., more usually from about 35° C. to 70° C., particularly 65° C.

The hybridization reactions are usually done in an aqueous medium, particularly a buffered aqueous medium, which may include various additives. Additives which may be employed include low concentrations of detergent (0.01 to 1%), salts, e.g., sodium citrate (0.017 to 0.17M), Ficoll, polyvinylpyrrolidone, carrier nucleic acids, carrier proteins, etc. Nonaqueous solvents may be added to the aqueous medium, such as dimethylformamide, dimethylsulfoxide, alcohols, and formamide. These other solvents are generally present in amounts ranging from 2 to 50%.

The stringency of the hybridization medium may be controlled by temperature, salt concentration, solvent system, and the like. Thus, depending upon the length and nature of the sequence of interest, the stringency will be varied.

Depending upon the nature of the label, various techniques can be employed for detecting the presence of the label. For fluorescers, a large number of different fluorometers are available. For chemiluminescers, luminometers or films are available. With enzymes, a fluorescent, chemiluminescent, or colored product can be provided and determined fluorometrically, luminometrically, spectrophotometrically or visually. The various labels which have been employed in immunoassays and the techniques applicable to immunoassays can be employed with the subject assays.

Kits for carrying out amplified nucleic acid hybridization assays according to the invention will comprise in packaged combination the following reagents: the amplifier probe or set of probes; the capture probe or set of probes; the amplifier multimer; and an appropriate labeled oligonucleotide. These reagents will typically be in separate containers in the kit. The kit may also include a denaturation reagent for denaturing the analyte, hybridization buffers, wash solutions, enzyme substrates, negative and positive controls and written instructions for carrying out the assay.

The following examples further illustrate the invention. These examples are not intended to limit the invention in any manner.

EXAMPLES

Example I

Synthesis of Comb-Type Branched Polynucleotide

This example illustrates the synthesis of a comb-type branched polynucleotide having 15 branch sites and sidechain extensions having three labeled probe binding sites. This polynucleotide was designed to be used in a solution phase hybridization as described in EPA 883096976, which published as EP 0317077 on May 24, 1989, the disclosure of which is also found in U.S. Pat. No. 5,124,246 which issued on Jun. 23, 1992.

All chemical syntheses of oligonucleotides were performed on an automatic DNA synthesizer (Applied Biosystems, Inc., (ABI) model 380 B). Phosphoramidite chemistry of the beta cyanoethyl type was used including 5'-phosphorylation which employed Phostel™ reagent (DMT-O—CH$_2$CH$_2$—(SO$_2$)—CH$_2$CH$_2$—O—P(—N(iPr)$_2$)(—O—CH$_2$CH$_2$CN) wherein DMT is dimethoxytrityl and iPr is isopropyl) (ABN).

Standard ABI protocols were used except as indicated. Where it is indicated that a multiple of a cycle was used (e.g., 1.2 cycle), the multiple of the standard amount of amidite recommended by ABI was employed in the specified cycle. Appended hereto are the programs for carrying out cycles 1.2 and 6.4 as run on the Applied Biosystems Model 380 B DNA Synthesizer.

A comb body of the following structure was first prepared:

3'T$_{18}$(TTX')$_{15}$GTTTGTGG-5'
|
(RGTCAGTp-5')$_{15}$ wherein X' is a branching monomer, and R is a periodate cleavable linker.

The portion of the comb body through the 15 (TTX') repeats is first synthesized using 33.8 mg aminopropyl-derivatized thymidine controlled pore glass (CPG) (2000 Å, 7.4 micromoles thymidine per gram support) with a 1.2 cycle protocol. The branching site nucleotide was of the formula:

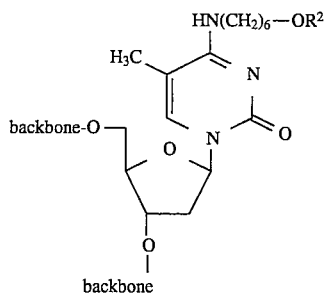

where R$^2$ represents

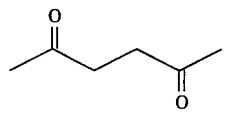

For synthesis of the comb body (not including sidechains), the concentration of beta cyanoethylphosphoramidite monomers was 0.1M for A, C, G and T, 0.15M for the branching site monomer E, and 0.2M for Phostel™ reagent (DMT—O—CH$_2$CH$_2$—(SO$_2$)—CH$_2$CH$_2$—O—P(—N(iPr)$_2$)(—O—CH$_2$CH$_2$CN) wherein DMT is dimethoxytrityl and iPr is isopropyl). Detritylation was done with 3% trichloroacetic acid in methylene chloride using stepped flowthrough for the duration of the deprotection. At the conclusion the 5' DMT was replaced with an acetyl group.

Cleavable linker R and six base sidechain extensions of the formula 3'-RGTCAGTp (SEQ ID NO:1) were synthesized at each branching monomer site as follows. The base protecting group removal (R$^2$ in the formula above) was performed manually while retaining the CPG support in the same column used for synthesizing the comb body. In the case of R$^2$=levulinyl, a solution of 0.5M hydrazine hydrate in pyridine/glacial acetic acid (1:1 v/v) was introduced and kept in contact with the CPG support for 90 min with renewal of the liquid every 15 min, followed by extensive washing with pyridine/glacial acetic acid (1:1 v/v) and then by acetonitrile. After the deprotection the cleavable linker R and six base sidechain extensions were added using a 6.4 cycle.

In these syntheses the concentration of phosphoramidites was 0.1M (except 0.2M R and Phostel™ reagent (DMT—O—CH$_2$CH$_2$—(SO$_2$)—CH$_2$CH$_2$—O—P(—N(iPr)$_2$)(—O—CH$_2$CH$_2$CN) wherein DMT is dimethoxytrityl and iPr is isopropyl); R was 2-(4-(4-(2-Dimethoxytrityloxy)ethyl-)phenoxy 2,3-di(benzoyloxy)-butyloxy)phenyl)ethyl-2-cyanoethyl-N,N-diisopropylphosphoramidite).

Detritylation is effected with a solution of 3% trichloroacetic acid in methylene chloride using continuous flowthrough, followed by a rinse solution of toluene/chloromethane (1:1 v/v). Branched polynucleotide chains were removed from the solid supports automatically in the 380B using the cycle "CE NH$_3$." The ammonium hydroxide solution was collected in 4 ml screw-capped Wheaton vials and heated at 60° C. for 12 hr to remove all base-protecting groups. After cooling to room temperature the solvent was removed in a Speed-Vac evaporator and the residue dissolved in 100 μl water.

3' backbone extensions (segment A), sidechain extensions and ligation template/linkers of the following structures were also made using the automatic synthesizer:

| | |
|---|---|
| 3' Backbone extension | 3'-TCCGTATCCTGGGCACAGAGGTGCp-5' (SEQ ID NO:2) |
| Sidechain extension | 3'-GATGCG(TTCATGCTGTTGGTGTAG)₃-5' (SEQ ID NO:3) |
| Ligation template for linking 3' backbone extension | 3'-AAAAAAAAAAGCACCTp-5' (SEQ ID NO:4) |
| Ligation template for linking sidechain extension | 3'-CGCATCACTGAC-5' (SEQ ID NO:5) |

The crude comb body was purified by a standard polyacrylamide gel (7% with 7M urea and IX TBE running buffer) method.

The 3' backbone extension and the sidechain extensions were ligated to the comb body as follows. The comb body (4 pmole/μl), 3' backbone extension (6.25 pmole/μl), sidechain extension (93.75 pmole/μl), sidechain linking template (75 pmoles/μl) and backbone linking template (5 pmole/μl) were combined in 1 mM ATP/5 mM DTT/50 mM Tris-HCl, pH 8.0/10 mM $MgCl_2$/ 2 mM spermidine, with 0.5 units/μl T4 polynucleotide kinase. The mixture was incubated at 37° C. for 2 hr, then heated in a water bath to 95° C., and then slowly cooled to below 35° C. over a 1 hr period. 2 mM ATP, 10 mM DTT, 14% polyethylene glycol, and 0.21 units/μl T4 ligase were added, and the mixture incubated for 16–24 hr at 23° C. The DNA was precipitated in NaCl/ethanol, resuspended in water, and subjected to a second ligation as follows. The mixture was adjusted to 1 mM ATP, 5 mM DTT, 14% polyethylene glycol, 50 mM Tris-HCl, pH 7.5, 10 mM $MgCl_2$, 2 mM spermidine, 0.5 units/μl T4 polynucleotide kinase, and 0.21 units/μl T4 ligase were added, and the mixture incubated at 23° C. for 16–24 hr. Ligation products were then purified by polyacrylamide gel electrophoresis.

After ligation and purification, a portion of the product was labeled with $^{32}p$ and subjected to cleavage at the site of R achieved by oxidation with aqueous $NaIO_4$ for 1 hr. The sample was then analyzed by PAGE to determine the number of sidechain extensions incorporated by quantitating the radioactive label in the bands on the gel. The product was found to have a total of 45 labeled probe binding sites.

Example II

DNA Hybridization Assay for Chlamydiae

A "5×1" amplified solution phase nucleic acid sandwich hybridization assay format was employed in this example. The "5×1" designation derives from the fact that the format employs two multimers: (1) an amplifier probe having a first segment (A) that binds to Chlamydiae DNA and a second segment (B) that hybridizes to (2) an amplifier multimer having a first segment (B*) that hybridizes to the segment (B) and five iterations of a segment (C) that hybridizes to a labeled oligonucleotide (label probe).

A "15×3" amplified solution phase nucleic acid sandwich hybridization assay format may also be used. The "15×3" designation derives from the fact that the format employs two multimers: (1) an amplifier probe having a first segment (A) that binds to Chlamydiae and a second segment (B) that hybridizes to (2) an amplifier multimer having a first segment (B*) that hybridizes to the segment (B) and fifteen iterations of a segment (C), wherein segment C hybridizes to three labeled oligonucleotides.

The amplifier and capture probe segments used in this assay were as follows. Two sets of probes were designed, the first set consisting of the capture and amplifier probes disclosed in EP 883096976, which published as EP 0317077 on May 24, 1989, the disclosure of which is also found in U.S. Pat. No. 5,124,246 which issued on Jun. 23, 1992, plus an additional 32 oligonucleotide sequences as capture or amplifier probes. The second, alternate set of probes consisted of further oligonucleotide sequences for use as capture probes, such that these new capture probe sequences lie on the plasmid between the EP 883096976 probes and the new set of 32 oligonucleotides described above, and the use of the capture probes from first set described above as amplifier probes in addition to the new amplifier probes of set I. These sequences, with descriptive names, are listed below.

Chlamydiae Set I

Amplifier probes

Chlaplkit1.2 (SEQ ID NO:5) TTCTTTAGATTTCTTAGT-TATTTCTTCAAA

Chlaplkit1.3 (SEQ ID NO:6) CTCTTTATTTAGATATA-GAATTTCTTTTTT

Chlaplkit1.4 (SEQ ID NO:7) GAGTTTAGAAGAATCCA-GAAATTCAATGCG

Chlaplkit1.6 (SEQ ID NO:8) TTCTATACATTTATCGAT-AGCTAACTCGAT

Chlaplkit1.7 (SEQ ID NO:9) TTTCCAGTTCCTTGTA-CAAATGTACCGATT

Chlaplkit1.8 (SEQ ID NO:10) CCTTAAAATATATGCAA-GACTTTTAACGTT

Chlaplkit1.10 (SEQ ID NO:11) CTTAGT-TAATTTTCGTCTCTTTTTCGCAGC

Chlaplkit1.11 (SEQ ID NO:12) TGTAATCACCCAGTC-GATAAATGTGTAAGC

Chlaplkit1.12 (SEQ ID NO:13) CTTTGATGCATTTGG-GAAGCGCATTTTTAT

Chlaplkit1.14 (SEQ ID NO:14) GGATTCTATTTGATC-TACCAAGATAGGACA

Chlaplkit1.15 (SEQ ID NO:15) CTCTACAACGAAC-CCTTTATGTTTCCGTGT

Chlaplkit1.16 (SEQ ID NO:16) TGGTGAATTAAAAGGT-GTTAAGTCTATATC

Chlaplkit1.18 (SEQ ID NO:17) GTAAATCCTAATGATCG-GAGAAAGAGTTTG

Chlaplkit1.19 (SEQ ID NO:18) ACGGTCTACTATTTGT-GTTCCATTAGTCCA

Chlaplkit1.20 (SEQ ID NO:19) AGTTCTAGTTGCCAC-TATTAAAAACGGTTG

Chlaplkit1.22 (SEQ ID NO:20) AGCTTCTTTTCCAC-TAAACTCATACTTATT

Chlaplkit1.23 (SEQ ID NO:21) GGATGTTTTATACCGCT-TAACTCCATAAGC

Chlaplkit1.24 (SEQ ID NO:22) TAAGAAT-TCAGTTTTTGTAAAACGGATTCT

Chlaplkit1.26 (SEQ ID NO:23) TCTGGATAAAACAAC-CCCTTTTGTGTTCCC

Chlaplkit1.27 (SEQ ID NO:24) GTAATTCGTTGCAGT-CAGCAATCTTTGGAT

Chlaplkit1.28 (SEQ ID NO:25) TGCTAATGCATGGTAAT-GAGATGAAAGAAA

Chlaplkit1.30 (SEQ ID NO:26) CAATTTGGGAGATATCT-TAATAGATTGACC

Chlaplkit1.31 (SEQ ID NO:27) TCTTCTTCCAAACTTCT-GATTTTCAAGGTG

Chlaplkit1.32 (SEQ ID NO:28) AGGACTTTTGAT-GAAGTGGCAGTTACTATA pCHL2.CLLA2C-2 (SEQ ID NO:29) TTCTTCAGCGCTA-CACACGCTCAAATCATC pCHL2.CLLA2C-3 (SEQ ID NO:30) ATTAAACGAGCG-GAAAATGAAATTACTCAA pCHL2.CLLA2C-4 (SEQ ID NO:31) CGGAGATCTACG-CAATGGATTTTCATTGTA pCHL2.CLLA2C-6 (SEQ ID NO:32) GCGAATA-GAAAAAGTCTTTGCTATAGCACT pCHL2.CLLA2C-7 (SEQ ID NO:33) GAATATATCAT-AAATAGACCGGCCTCTAGC pCHL2.CLLA2C-8 (SEQ ID NO:34) TATACGAGCCAG-CACTCCAATTTCTGACTG pCHL2.CLLA2C-10 (SEQ ID NO:35) GTATCCTGTTGG-GAAGGCATCAAAGAAAGA pCHL2.CLLA2C-12 (SEQ ID NO:36) TGGCCTAGCTGC-TATAATCACGAAATTACC pCHL2.CLLA2C-11 (SEQ ID NO:37) AGCTAA-GATAACTCCTTTATCATCAATATC pCHL2.CLLA2C-14 (SEQ ID NO:38) TCTACGCTGT-TGAGTAACCGCAAGATTTAT pCHL2.CLLA2C-15 (SEQ ID NO:39) ACCTGCGCT-CATTTCTAGAGATAGGAAACC pCHL2.CLLA2C-16 (SEQ ID NO:40) TGTTAAATTAG-CAATAATCCGCTCAACAAT pCHL2. CLLA2C-18 ( SEQ ID NO: 41 ) TTCTTC-TACTCGGAATAATTCTTCTTTAGA pCHL2.CLLA2C-19 (SEQ ID NO:42) ATAAAAATGT-GATTCTCTAACTGTTTCTCC Capture Probes Chlaplkit1.1 (SEQ ID NO:43) ATTAATAGATTCTTGT-TCTAATTGTTCCAT Chlaplkit1.5 (SEQ ID NO:44) TCTTCTAGATAACCAAC-CAAGCTGAATGGC Chlaplkit1.9 (SEQ ID NO:45) GTTTAAGAA-CAAGTTTTCTGGCCAAGAATT Chlaplkit1.13 (SEQ ID NO:46) TTGGTATACATTTGCAG-GCTTGATTACAAA Chlaplkit1.17 (SEQ ID NO:47) ATTTTCTTCGTCAGT-TAAACCTTCCCATCC Chlaplkit1.21 (SEQ ID NO:48) TCCTAAATGGTATAAG-GCTTCTAAAGCAGT Chlaplkit1.25 (SEQ ID NO:49) TATCCATCCTTCAAAT-TGAAAACTATTTGA Chlaplkit1.29 (SEQ ID NO:50) AAGACCTATAACTTC-TACCATCCCATTTTG pCHL2.CXTI-1 (SEQ ID NO:51) GAAAACCGTAT-GAGAAACGGATCTAAGCTT pCHL2.CXTI-5 (SEQ ID NO:52) AAGCCTTCCCTT-TATACGCTCAAGCAATAG pCHL2.CXTI-9 (SEQ ID NO:53) TTGATTCTCA-GAGAACGTTGCTCGTCTTTT pCHL2.CXTI-17 (SEQ ID NO:54) ATCCCCTCTTTG-TAATTTTTCACCAGATAT Chlamydiae Probes Set II Amplifier Probes Chlaplkit21.1 (SEQ ID NO:55) ATTAATAGATTCTTGT-TCTAATTGTTCCAT Chlaplkit21.5 (SEQ ID NO:56) TCTTCTAGATAAC-CAACCAAGCTGAATGGC Chlaplkit21.9 (SEQ ID NO:57) GTTTAAGAA-CAAGTTTTCTGGCCAAGAATT Chlaplkit21.13 (SEQ ID NO:58) TTGGTATACATTTG-CAGGCTTGATTACAAA Chlaplkit21.17 (SEQ ID NO:59) ATTTTCTTCGTCAGT-TAAACCTTCCCATCC Chlaplkit21.21 (SEQ ID NO:60) TCCTAAATGGTATAAG-GCTTCTAAAGCAGT Chlaplkit21.25 (SEQ ID NO:61) TATCCATCCTTCAAAT-TGAAAACTATTTGA Chlaplkit21.29 (SEQ ID NO:62) AAGACCTATAACTTC-TACCATCCCATTTTG Chlaplkit1.2 (SEQ ID NO:5) TTCTTTAGATTTCTTAGT-TATTTCTTCAAA Chlaplkit1.3 (SEQ ID NO:6) CTCTTTATTTAGATATA-GAATTTCTTTTTT Chlaplkit1.4 (SEQ ID NO:7) GAGTTTAGAAGAATCCA-GAAATTCAATGCG Chlaplkit1.6 (SEQ ID NO:8) TTCTATACATTTATCGAT-AGCTAACTCGAT Chlaplkit1.7 (SEQ ID NO:9) TTTCCAGTTCCTTGTA-CAAATGTACCGATT Chlaplkit1.8 (SEQ ID NO:10) CCTTAAAATATATGCAA-GACTTTTAACGTT Chlaplkit1.10 (SEQ ID NO:11) CTTAGT-TAATTTTCGTCTCTTTTTCGCAGC Chlaplkit1.11 (SEQ ID NO:12) TGTAATCACCCAGTC-GATAAATGTGTAAGC Chlaplkit1.12 (SEQ ID NO:13) CTTTGATGCATTTGG-GAAGCGCATTTTTAT Chlaplkit1.14 (SEQ ID NO:14) GGATTCTATTTGATC-TACCAAGATAGGACA Chlaplkit1.15 (SEQ ID NO:15) CTCTACAACGAAC-CCTTTATGTTTCCGTGT Chlaplkit1.16 (SEQ ID NO:16) TGGTGAATTAAAAGGT-GTTAAGTCTATATC Chlaplkit1.18 (SEQ ID NO:17) GTAAATCCTAATGATCG-GAGAAAGAGTTTG Chlaplkit1.19 (SEQ ID NO:18) ACGGTCTACTATTTGT-GTTCCATTAGTCCA Chlaplkit1.20 (SEQ ID NO:19) AGTTCTAGTTGCCAC-TATTAAAAACGGTTG Chlaplkit1.22 (SEQ ID NO:20) AGCTTCTTTTCCAC-TAAACTCATACTTATT Chlaplkit1.23 (SEQ ID NO:21) GGATGTTTTATACCGCT-TACTCCATAAGC Chlaplkit1.24 (SEQ ID NO:22) TAAGAAT-TCAGTTTTTGTAAAACGGATTCT Chlaplkit1.26 (SEQ ID NO:23) TCTGGATAAAACAAC-CCCTTTTGTGTTCCC Chlaplkit1.27 (SEQ ID NO:24) GTAATTCGTTGCAGT-CAGCAATCTTTGGAT Chlaplkit1.28 (SEQ ID NO:25) TGCTAATGCATGGTAAT-GAGATGAAAGAAA Chlaplkit1.30 (SEQ ID NO:26) CAATTTGGGAGATATCT-TAATAGATTGACC Chlaplkit1.31 (SEQ ID NO:27) TCTTCTTCCAAACTTCT-GATTTCAAGGTG Chlaplkit1.32 (SEQ ID NO:28) AGGACTTTTGAT-GAAGTGGCAGTTACTATA Capture Probes Chlaplkit2C.1 (SEQ ID NO:63) ACTTTTTTAATAGCG-GAGAATTTACTAATT Chlaplkit2C.2 (SEQ ID NO:64) GGATCGAAATG-TAATACCGAAGAGAAAACC Chlaplkit2C.3 (SEQ ID NO:65) CCATGTCTATTTTC-CCAACAGTTATCTCA Chlaplkit2C.4 (SEQ ID NO:66) TTAGAAGACGATTCCT-TCCTATTGATAAAC Chlaplkit2C.5 (SEQ ID NO:67) ATCA CATCTGCGTCT-TGCTCT ATTTGA CCG Chlaplkit2C.6 (SEQ ID NO:68) TCTCGCAAATCT-GAAAGCATGGGAACTTTA Chlaplkit2C.7 (SEQ ID NO:69) GCTCTATCCT-CAACTTTTCTAGATAGTTGG Chlaplkit2C.8 (SEQ ID NO:70) AAACAAACTATAG-GAATGTTTAGCTCTGAG Chlaplkit2C.9 (SEQ ID NO:71) AAACCTCTTAAGGT-TCTAGATATATCTGCT Chlaplkit2C.10 (SEQ ID NO:72) TCATTTTGAC-GATTTTCTCCAACCGATGAG Chlaplkit2C.11 (SEQ ID NO:73) ATCAACTGCAAG-TAATCGATAAATATTACG Chlaplkit2C.12 (SEQ ID NO:74) ACTCGATCT-TCTTTTCTCAGCAACCGGATC Thus, each amplifier probe contained, in addition to the sequences substantially complementary to the Chlamydiae sequences, a 3' extension complementary to a segment of the amplifier multimer,

AGGCATAGGACCCGTGTCTT (SEQ ID NO:75).

Each capture probe contained, in addition to the sequences substantially complementary to Chlamydiae DNA, a downstream sequence complementary to DNA bound to the solid phase is complementary to (XTI*),

CTTCTTTGGAGAAAGTGGTG (SEQ ID NO:76).

Microtiter plates were prepared as follows. White Microlite 1 Removawell strips (polystyrene microtiter plates, 96 wells/plate) were purchased from Dynatech Inc. Each well was filled with 200 µl 1N HCl and incubated at room temperature for 15–20 min. The plates were then washed 4 times with 1×PBS and the wells aspirated to remove liquid. The wells were then filled with 200 µl 1N NaOH and incubated at room temperature for 15–20 min. The plates were again washed 4 times with 1×PBS and the wells aspirated to remove liquid.

Poly(phe-lys) was purchased from Sigma Chemicals, Inc. This polypeptide has a 1:1 molar ratio of phe:lys and an average m.w. of 47,900 gm/mole. It has an average length of 309 amino acids and contains 155 amines/mole. A 1 mg/ml solution of the polypeptide was mixed with 2M NaCl/1× PBS to a final concentration of 0.1 mg/ml (pH 6.0). 100 µL of this solution was added to each well. The plate was wrapped in plastic to prevent drying and incubated at 30° C. overnight. The plate was then washed 4 times with 1× PBS and the wells aspirated to remove liquid.

The following procedure was used to couple the oligonucleotide XTI* to the plates. Synthesis of XT1* was described in EPA 883096976. 20 mg disuccinimidyl suberate was dissolved in 300 µl dimethyl formamide (DMF). 26 OD260 units of XT1, was added to 100µl coupling buffer (50 mM sodium phosphate, pH 7.8). The coupling mixture was then added to the DSS-DMF solution and stirred with a magnetic stirrer for 30 min. An NAP-25 column was equilibrated with 10 mM sodium phosphate, pH 6.5. The coupling mixture DSS-DMF solution was added to 2 ml 10 mM sodium phosphate, pH 6.5, at 4° C. The mixture was vortexed to mix and loaded onto the equilibrated NAP-25 column. DSS-activated XT1, DNA was eluted from the column with 3.5 ml 10 mM sodium phosphate, pH 6.5. 5.6 OD260 units of eluted DSS-activated XT1* DNA was added to 1500 ml 50 mM sodium phosphate, pH 7.8. 50µl of this solution was added to each well and the plates were incubated overnight. The plate was then washed 4 times with IX PBS and the wells aspirated to remove liquid.

Final stripping of plates was accomplished as follows. 200 µL of 0.2N NaOH containing 0.5% (w/v) SDS was added to each well. The plate was wrapped in plastic and incubated at 65° C. for 60 min. The plate was then washed 4 times with 1× PBS and the wells aspirated to remove liquid. The stripped plate was stored with desiccant beads at 2°–8° C.

Sample preparation consisted of delivering serial dilutions of elementary bodies (EB) to each well corresponding to a range of from $3.1 \times 10^{-3}$ to $10^{-5}$ EB/well in 10µl extraction buffer (10 mM Tris-HCl, pH 8.0/0.15M NaCl/10 mM EDNA, pH 8.0/1% SDS/40 µg/ml sonicated salmon sperm DNA). Proteinase K in 13 µl extraction buffer (4 mg proteinase K in 4 ml extraction buffer) was added to each well. Plates were covered and agitated to mix samples, then incubated at 65° C. for 30 min to release nucleic acids.

A cocktail of the Chlamydiae-specific amplifier and capture probes listed above (Set I) was added to each well (5 fmoles/well). Plates were covered and gently agitated to mix reagents and then incubated at 65° C. for 30 min. Plates were removed from the incubator and cooled 10 min at room temperature.

Neutralization buffer was then added to each well (13µl of 0.77M 3-(N-morpholino)propane sulfonic acid/1.845M NaCl/0.185M sodium citrate). Plates were covered and incubated for 2–4 hr at 65° C.

After a further 10 min incubation at room temperature, the contents of each well were aspirated to remove all fluid, and the wells washed 2× with washing buffer (0.1% SDS/ 0.015M NaCl/0.0015M sodium citrate).

Amplifier multimer was then added to each well (100 fmoles/well). After covering plates and agitating to mix the contents in the wells, the plates were incubated for 30 min at 55° C. The contents were then immediately aspirated and the plates washed 2× as above.

Alkaline phosphatase label probe, disclosed in EP 883096976, was then added to each well (20 fmoles in 40 µl/well). After incubation at 55° C. for 15 min, the wells were washed twice as above and then 3× with 0.015M NaCl/0.0015M sodium citrate.

An enzyme-triggered dioxetane (Schaap et al., Tet. Lett. 191987) 28:1159–1162 and EPA Pub. No. 0254051, obtained from Lumigen, Inc., was employed. The detection procedure was as follows. 30µl Lumiphos 530 (Lumigen) was added to each well. The wells were tapped lightly so that the reagent would fall to the bottom and gently swirled to distribute the reagent evenly over the bottom. The wells were covered and incubated at 37° C. for 40 min.

Plates were then read on a Dynatech ML 1000 luminometer. Output was given as the full integral of the light produced during the reaction.

Results are shown in the Table below. Results for each standard sample are expressed as the difference between the mean of the negative control plus two standard deviations and the mean of the sample minus two standard deviations (delta). If delta is greater than zero, the sample is considered positive. These results indicate a sensitivity of about $10^4$ EBs.

TABLE

| #EB | Signal | Standard Deviation | Δ |
|---|---|---|---|
| $1 \times 10^6$ | 65.33 | 5.16 | 55.01 |
| $1 \times 10^5$ | 11.96 | 0.99 | 7.74 |
| $5 \times 10^4$ | 7.54 | 1.61 | 2.08 |
| $2.5 \times 10^4$ | 3.71 | 0.16 | 1.15 |

TABLE-continued

| #EB | Signal | Standard Deviation | Δ |
|---|---|---|---|
| $1.25 \times 10^4$ | 2.83 | 0.13 | 0.33 |
| $6 \times 10^3$ | 2.28 | 0.32 | −0.6 |
| $3 \times 10^3$ | 1.72 | 0.2 | −0.92 |
| $1.5 \times 10^3$ | 1.64 | 0.2 | −0.84 |
| 0 | 1.44 | 0.4 | — |

Modifications of the above-described modes for carrying out the invention that are obvious to those of skill in biochemistry, nucleic acid hybridization assays, and related fields are intended to be within the scope of the following claims.

SEQUENCE LISTING ( 1 ) GENERAL INFORMATION:

( i i i ) NUMBER OF SEQUENCES: 77

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CGTGGAGACA CGGGTCCTAT GCCT    24

( 2 ) INFORMATION FOR SEQ ID NO:2:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GATGTGGTTG TCGTACTTGA TGTGGTTGTC GTACTTGATG TGGTTGTCGT ACTTGCGTAG    60

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TCCACGAAAA AAAAAA    16

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CAGTCACTAC GC    12

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single ( D ) TOPOLOGY: linear ( x i ) SEQUENCE DESCRIPTION: SEQ ID NO:5:

TTCTTTAGAT TTCTTAGTTA TTTCTTCAAA 30

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CTCTTTATTT AGATATAGAA TTTCTTTTTT 30

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GAGTTTAGAA GAATCCAGAA ATTCAATGCG 30

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TTCTATACAT TTATCGATAG CTAACTCGAT 30

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TTTCCAGTTC CTTGTACAAA TGTACCGATT 30

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CCTTAAAATA TATGCAAGAC TTTTAACGTT 30

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CTTAGTTAAT TTTCGTCTCT TTTTCGCAGC 30

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

TGTAATCACC CAGTCGATAA ATGTGTAAGC 30

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

CTTTGATGCA TTTGGGAAGC GCATTTTTAT 30

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GGATTCTATT TGATCTACCA AGATAGGACA 30

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CTCTACAACG AACCCTTTAT GTTTCCGTGT 30

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

TGGTGAATTA AAAGGTGTTA AGTCTATATC 30

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GTAAATCCTA ATGATCGGAG AAAGAGTTTG 30

( 2 ) INFORMATION FOR SEQ ID NO:18:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

ACGGTCTACT ATTTGTGTTC CATTAGTCCA 30

( 2 ) INFORMATION FOR SEQ ID NO:19:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

AGTTCTAGTT GCCACTATTA AAAACGGTTG 30

( 2 ) INFORMATION FOR SEQ ID NO:20:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

AGCTTCTTTT CCACTAAACT CATACTTATT 30

( 2 ) INFORMATION FOR SEQ ID NO:21:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

GGATGTTTTA TACCGCTTAA CTCCATAAGC 30

( 2 ) INFORMATION FOR SEQ ID NO:22:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

TAAGAATTCA GTTTTTGTAA AACGGATTCT 30

( 2 ) INFORMATION FOR SEQ ID NO:23:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

TCTGGATAAA ACAACCCCTT TTGTGTTCCC 30

( 2 ) INFORMATION FOR SEQ ID NO:24:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:24:

GTAATTCGTT GCAGTCAGCA ATCTTTGGAT     30

( 2 ) INFORMATION FOR SEQ ID NO:25:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:25:

TGCTAATGCA TGGTAATGAG ATGAAAGAAA     30

( 2 ) INFORMATION FOR SEQ ID NO:26:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:26:

CAATTTGGGA GATATCTTAA TAGATTGACC     30

( 2 ) INFORMATION FOR SEQ ID NO:27:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:27:

TCTTCTTCCA AACTTCTGAT TTTCAAGGTG     30

( 2 ) INFORMATION FOR SEQ ID NO:28:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:28:

AGGACTTTTG ATGAAGTGGC AGTTACTATA     30

( 2 ) INFORMATION FOR SEQ ID NO:29:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:29:

TTCTTCAGCG CTACACACGC TCAAATCATC     30

( 2 ) INFORMATION FOR SEQ ID NO:30:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:30:

ATTAAACGAG CGGAAAATGA AATTACTCAA 30

( 2 ) INFORMATION FOR SEQ ID NO:31:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:31:

CGGAGATCTA CGCAATGGAT TTTCATTGTA 30

( 2 ) INFORMATION FOR SEQ ID NO:32:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:32:

GCGAATAGAA AAAGTCTTTG CTATAGCACT 30

( 2 ) INFORMATION FOR SEQ ID NO:33:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:33:

GAATATATCA TAAATAGACC GGCCTCTAGC 30

( 2 ) INFORMATION FOR SEQ ID NO:34:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:34:

TATACGAGCC AGCACTCCAA TTTCTGACTG 30

( 2 ) INFORMATION FOR SEQ ID NO:35:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:35:

GTATCCTGTT GGGAAGGCAT CAAAGAAAGA 30

( 2 ) INFORMATION FOR SEQ ID NO:36:

( i ) SEQUENCE CHARACTERISTICS:

(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:36:

TGGCCTAGCT GCTATAATCA CGAAATTACC  30

(2) INFORMATION FOR SEQ ID NO:37:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:37:

AGCTAAGATA ACTCCTTTAT CATCAATATC  30

(2) INFORMATION FOR SEQ ID NO:38:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:38:

TCTACGCTGT TGAGTAACCG CAAGATTTAT  30

(2) INFORMATION FOR SEQ ID NO:39:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:39:

ACCTGCGCTC ATTTCTAGAG ATAGGAAACC  30

(2) INFORMATION FOR SEQ ID NO:40:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:40:

TGTTAAATTA GCAATAATCC GCTCAACAAT  30

(2) INFORMATION FOR SEQ ID NO:41:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:41:

TTCTTCTACT CGGAATAATT CTTCTTTAGA  30

(2) INFORMATION FOR SEQ ID NO:42:

(i) SEQUENCE CHARACTERISTICS:
(A) LENGTH: 30 base pairs
(B) TYPE: nucleic acid

```
              ( C ) STRANDEDNESS: single
              ( D ) TOPOLOGY: linear ( x i ) SEQUENCE DESCRIPTION: SEQ ID NO:42:

ATAAAAATGT GATTCTCTAA CTGTTTCTCC                                                    30

( 2 ) INFORMATION FOR SEQ ID NO:43:

( i ) SEQUENCE CHARACTERISTICS:
              ( A ) LENGTH: 30 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:43:

ATTAATAGAT TCTTGTTCTA ATTGTTCCAT                                                    30

( 2 ) INFORMATION FOR SEQ ID NO:44:

( i ) SEQUENCE CHARACTERISTICS:
              ( A ) LENGTH: 30 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:44:

TCTTCTAGAT AACCAACCAA GCTGAATGGC                                                    30

( 2 ) INFORMATION FOR SEQ ID NO:45:

( i ) SEQUENCE CHARACTERISTICS:
              ( A ) LENGTH: 30 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:45:

GTTTAAGAAC AAGTTTTCTG GCCAAGAATT                                                    30

( 2 ) INFORMATION FOR SEQ ID NO:46:

( i ) SEQUENCE CHARACTERISTICS:
              ( A ) LENGTH: 30 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:46:

TTGGTATACA TTTGCAGGCT TGATTACAAA                                                    30

( 2 ) INFORMATION FOR SEQ ID NO:47:

( i ) SEQUENCE CHARACTERISTICS:
              ( A ) LENGTH: 30 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:47:

ATTTTCTTCG TCAGTTAAAC CTTCCCATCC                                                    30

( 2 ) INFORMATION FOR SEQ ID NO:48:

( i ) SEQUENCE CHARACTERISTICS:
              ( A ) LENGTH: 30 base pairs
              ( B ) TYPE: nucleic acid
              ( C ) STRANDEDNESS: single
              ( D ) TOPOLOGY: linear
```

(x i) SEQUENCE DESCRIPTION: SEQ ID NO:48:

TCCTAAATGG TATAAGGCTT CTAAAGCAGT 30

(2) INFORMATION FOR SEQ ID NO:49:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (x i) SEQUENCE DESCRIPTION: SEQ ID NO:49:

TATCCATCCT TCAAATTGAA AACTATTTGA 30

(2) INFORMATION FOR SEQ ID NO:50:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (x i) SEQUENCE DESCRIPTION: SEQ ID NO:50:

AAGACCTATA ACTTCTACCA TCCCATTTG 30

(2) INFORMATION FOR SEQ ID NO:51:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (x i) SEQUENCE DESCRIPTION: SEQ ID NO:51:

GAAAACCGTA TGAGAAACGG ATCTAAGCTT 30

(2) INFORMATION FOR SEQ ID NO:52:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (x i) SEQUENCE DESCRIPTION: SEQ ID NO:52:

AAGCCTTCCC TTTATACGCT CAAGCAATAG 30

(2) INFORMATION FOR SEQ ID NO:53:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (x i) SEQUENCE DESCRIPTION: SEQ ID NO:53:

TTGATTCTCA GAGAACGTTG CTCGTCTTTT 30

(2) INFORMATION FOR SEQ ID NO:54:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (x i) SEQUENCE DESCRIPTION: SEQ ID NO:54:

ATCCCTCTT TGTAATTTTT CACCAGATAT 30

( 2 ) INFORMATION FOR SEQ ID NO:55:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

ATTAATAGAT TCTTGTTCTA ATTGTTCCAT 30

( 2 ) INFORMATION FOR SEQ ID NO:56:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

TCTTCTAGAT AACCAACCAA GCTGAATGGC 30

( 2 ) INFORMATION FOR SEQ ID NO:57:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

GTTTAAGAAC AAGTTTCTG GCCAAGAATT 30

( 2 ) INFORMATION FOR SEQ ID NO:58:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:58:

TTGGTATACA TTTGCAGGCT TGATTACAAA 30

( 2 ) INFORMATION FOR SEQ ID NO:59:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:59:

ATTTTCTTCG TCAGTTAAAC CTTCCCATCC 30

( 2 ) INFORMATION FOR SEQ ID NO:60:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:60:

TCCTAAATGG TATAAGGCTT CTAAAGCAGT 30

( 2 ) INFORMATION FOR SEQ ID NO:61:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:61:

TATCCATCCT TCAAATTGAA AACTATTTGA        30

( 2 ) INFORMATION FOR SEQ ID NO:62:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:62:

AAGACCTATA ACTTCTACCA TCCCATTTTG        30

( 2 ) INFORMATION FOR SEQ ID NO:63:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:63:

ACTTTTTTAA TAGCGGAGAA TTTACTAATT        30

( 2 ) INFORMATION FOR SEQ ID NO:64:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:64:

GGATCGAAAT GTAATACCGA AGAGAAAACC        30

( 2 ) INFORMATION FOR SEQ ID NO:65:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:65:

CCATGTCTAT TTTTCCCAAC AGTTATCTCA        30

( 2 ) INFORMATION FOR SEQ ID NO:66:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:66:

TTAGAAGACG ATTCCTTCCT ATTGATAAAC        30

( 2 ) INFORMATION FOR SEQ ID NO:67:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:67:

ATCACATCTG CGTCTTGCTC TATTTGACCG                                            30

( 2 ) INFORMATION FOR SEQ ID NO:68:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:68:

TCTCGCAAAT CTGAAAGCAT GGGAACTTTA                                            30

( 2 ) INFORMATION FOR SEQ ID NO:69:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:69:

GCTCTATCCT CAACTTTTCT AGATAGTTGG                                            30

( 2 ) INFORMATION FOR SEQ ID NO:70:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:70:

AAACAAACTA TAGGAATGTT TAGCTCTGAG                                            30

( 2 ) INFORMATION FOR SEQ ID NO:71:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:71:

AAACCTCTTA AGGTTCTAGA TATATCTGCT                                            30

( 2 ) INFORMATION FOR SEQ ID NO:72:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:72:

TCATTTTGAC GATTTCTCC AACCGATGAG                                             30

( 2 ) INFORMATION FOR SEQ ID NO:73:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:73:

ATCAACTGCA AGTAATCGAT AAATATTACG  30

( 2 ) INFORMATION FOR SEQ ID NO:74:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:74:

ACTCGATCTT CTTTTCTCAG CAACCGGATC  30

( 2 ) INFORMATION FOR SEQ ID NO:75:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:75:

AGGCATAGGA CCCGTGTCTT  20

( 2 ) INFORMATION FOR SEQ ID NO:76:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:76:

CTTCTTTGGA GAAAGTGGTG  20

( 2 ) INFORMATION FOR SEQ ID NO:77:

( i ) SEQUENCE CHARACTERISTICS:
    ( A ) LENGTH: 7 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:77:

TGACTGR  7

We claim:

1. A synthetic oligonucleotide useful as an amplifier probe in a sandwich hybridization assay for Chlamydiae, wherein said oligonucleotide consists of:
- a first segment having a minimum length of about 25 nucleotides and a maximum length of about 100 nucleotides which segment is at least 90% complementary to a segment of Chlamydiae plasmid DNA, wherein said first segment comprises a nucleotide sequence selected from the group consisting of SEQ ID NOS: 5–28 and 43–50; and
- a second segment consisting of a nucleotide sequence which is at least 90% complementary to an oligonucleotide segment of a nucleic acid multimer wherein said second segment is not complementary to Chlamydiae plasmid DNA;
- and optionally one or more noncomplementary segments each consisting of a nucleotide sequence that is not complementary to Chlamydiae plasmid DNA.

2. The synthetic oligonucleotide of claim 1, wherein said second segment comprises SEQ ID NO:75.

3. The synthetic oligonucleotide of claim 1, wherein said first segment consists of a nucleotide sequence selected from the group consisting of SEQ ID NOS: 5–28 and 43–50.

4. A synthetic oligonucleotide useful as a capture probe in a sandwich hybridization assay for Chlamydiae, wherein the synthetic oligonucleotide consists of:

a first segment having a minimum length of about 25 nucleotides and a maximum length of about 100 nucleotides which segment is at least 90% complementary to a segment of Chlamydiae plasmid DNA, wherein said first segment comprises a nucleotide sequence selected from the group consisting of SEQ ID NOS: 55–74; and a second segment consisting of a nucleotide sequence which is at least 90% complementary to an oligonucleotide bound to a solid phase wherein said second segment is not complementary to Chlamydiae plasmid DNA;

and optionally one or more noncomplementary segments each consisting of a nucleotide sequence that is not complementary to Chlamydiae plasmid DNA.

5. The synthetic oligonucleotide of claim 4, wherein said second segment comprises SEQ ID NO:76.

6. The synthetic oligonucleotide of claim 4, wherein said first segment consists of a nucleotide sequence selected from the group consisting of SEQ ID NOS: 55–74.

7. A set of synthetic oligonucleotides useful as amplifier probes in a sandwich hybridization assay for Chlamydiae, comprising at least two different oligonucleotide probes, wherein each oligonucleotide probe consists of:

a first segment having a minimum length of about 25 nucleotides and a maximum length of about 100 nucleotides which segment is at least 90% complementary to a segment of Chlamydiae plasmid DNA, wherein said first segment comprises a nucleotide sequence selected from the group consisting of SEQ ID NOS: 5–28 and 43–50; and a second segment consisting of a nucleotide sequence which is at least 90% complementary to an oligonucleotide segment of a nucleic acid multimer wherein said second segment is not complementary to Chlamydiae plasmid DNA;

and optionally one or more noncomplementary segments each consisting of a nucleotide sequence that is not complementary to Chlamydiae plasmid DNA.

8. The set of synthetic oligonucleotides of claim 7, wherein each said second segment comprises SEQ ID NO: 75.

9. The set of synthetic oligonucleotides of claim 7, wherein said set comprises at least five different oligonucleotide probes.

10. The set of synthetic oligonucleotides of claim 7, wherein each of said first segments consists of a nucleotide sequence selected from the group consisting of SEQ ID NOS: 5–28 and 43–50.

11. A kit for the detection of Chlamydiae in a sample comprising in combination (i) a set of amplifier probe oligonucleotides comprising the set of oligonucleotides of claim 7;

(ii) a set of capture probe oligonucleotides comprising at least two different oligonucleotides each of which consists of a first segment having a minimum length of about 25 nucleotides and a maximum length of about 100 nucleotides which segment is at least 90% complementary to a segment of Chlamydiae plasmid DNA, wherein said first segment comprises a nucleotide sequence selected from the group consisting of SEQ ID NOS: 55–74; and a second segment consisting of a nucleotide sequence which is at least 90% complementary to an oligonucleotide bound to a solid phase wherein said second segment is not complementary to Chlamydiae plasmid DNA;

and optionally one or more noncomplementary segments each consisting of a nucleotide sequence that is not complementary to Chlamydiae plasmid DNA;

(iii) a nucleic acid multimer, said multimer comprising at least one oligonucleotide segment that is at least 90% complementary to the second segment of the amplifier probe polynucleotide and a multiplicity of second oligonucleotide segments that are at least 90% complementary to a labeled oligonucleotide; and (iv) a labeled oligonucleotide.

12. The kit of claim 11, wherein said set of amplifier probes comprises at least five different oligonucleotide probes.

13. The kit of claim 11, wherein said set of capture probes comprises at least five different oligonucleotide probes.

14. A set of synthetic oligonucleotides useful as capture probes in a sandwich hybridization assay for Chlamydiae, comprising at least two different oligonucleotide probes, wherein each oligonucleotide probe consists of:

a first segment having a minimum length of about 25 nucleotides and a maximum length of about 100 nucleotides which segment is at least 90% complementary to a segment of Chlamydiae plasmid DNA, wherein said first segment comprises a nucleotide sequence selected from the group consisting of SEQ ID NOS: 55–74; and a second segment consisting of a nucleotide sequence which is at least 90% complementary to an oligonucleotide bound to a solid phase wherein said second segment is not complementary to Chlamydiae plasmid DNA;

and optionally one or more noncomplementary segments each consisting of a nucleotide sequence that is not complementary to Chlamydiae plasmid DNA.

15. The set of synthetic oligonucleotides of claim 14, wherein each said second segment comprises SEQ ID NO:76.

16. The set of synthetic oligonucleotides of claim 14, wherein said set comprises at least five different oligonucleotide probes.

17. The set of synthetic oligonucleotides of claim 14, wherein each of said first segments consists of a nucleotide sequence selected from the group consisting of SEQ ID NOS: 55–74.

18. A solution sandwich hybridization assay for detecting the presence of Chlamydiae in a sample, comprising (a) contacting the sample with (i) amplifier probes comprising the set of synthetic oligonucleotides of claim 29 and (ii) a set of capture probe oligonucleotides wherein there is a molar excess of amplifier probes and of capture probes over analyte nucleic acid in the sample, wherein said set of capture probe oligonucleotides comprises at least two different oligonucleotides each of which consists of a first segment having a minimum length of about 25 nucleotides and a maximum length of about 100 nucleotides which segment is at least 90% complementary to a segment of Chlamydiae nucleic acid, wherein said first segment comprises a nucleotide sequence selected from the group consisting of SEQ ID NOS: 55–74; and a second segment consisting of a nucleotide sequence which is at least 90% complementary to an oligonucleotide bound to a solid phase wherein said second segment is not complementary to Chlamydiae plasmid DNA;

and optionally one or more noncomplementary segments each consisting of a nucleotide sequence that is not complementary to Chlamydiae plasmid DNA;

(b) contacting the product of step (a) with said oligonucleotide bound to the solid phase;

(c) thereafter separating materials not bound to the solid phase;

(d) contacting the bound product of step (c) with a nucleic acid multimer, said multimer comprising at least one oligonucleotide segment that is at least 90% complementary to the second segment of the amplifier probe polynucleotide and a multiplicity of second oligonucleotide segments that are at least 90% complementary to a labeled oligonucleotide;

(e) removing unbound multimer;

(f) contacting the solid phase complex product of step (e) with the labeled oligonucleotide;

(g) removing unbound labeled oligonucleotide; and (h) detecting the presence of label in the solid phase complex product of step (g) and, thereby, detecting the presence of virus in the sample.

19. The assay of claim 18, wherein said set of amplifier probes comprises at least five different oligonucleotide probes.

20. The assay of claim 18, wherein said set of capture probes comprises at least five different oligonucleotide probes.

* * * * *